United States Patent
Hare et al.

(10) Patent No.: US 11,975,068 B2
(45) Date of Patent: May 7, 2024

(54) MESENCHYMAL STEM CELLS AS VACCINE ADJUVANTS AND METHODS FOR USING THE SAME

(71) Applicant: Longeveron Inc., Miami, FL (US)

(72) Inventors: Joshua M. Hare, Miami, FL (US); Ana Marie Landin, Coral Gables, FL (US)

(73) Assignee: LONGEVERON, INC., Miami, FL (US)

(*) Notice: Subject to any disclaimer, the term of this patent is extended or adjusted under 35 U.S.C. 154(b) by 0 days.

(21) Appl. No.: 16/075,276

(22) PCT Filed: Feb. 2, 2017

(86) PCT No.: PCT/US2017/016200
§ 371 (c)(1),
(2) Date: Aug. 3, 2018

(87) PCT Pub. No.: WO2017/136539
PCT Pub. Date: Aug. 10, 2017

(65) Prior Publication Data
US 2019/0038742 A1    Feb. 7, 2019

Related U.S. Application Data
(60) Provisional application No. 62/291,350, filed on Feb. 4, 2016.

(51) Int. Cl.
| | |
|---|---|
| *A61K 39/39* | (2006.01) |
| *A61K 35/28* | (2015.01) |
| *A61K 38/00* | (2006.01) |
| *A61K 39/00* | (2006.01) |
| *A61K 39/145* | (2006.01) |
| *A61P 31/16* | (2006.01) |

(52) U.S. Cl.
CPC .............. *A61K 39/39* (2013.01); *A61K 35/28* (2013.01); *A61K 39/145* (2013.01); *A61P 31/16* (2018.01); *A61K 38/00* (2013.01); *A61K 2039/515* (2013.01); *A61K 2039/5252* (2013.01); *A61K 2039/5254* (2013.01); *A61K 2039/54* (2013.01); *A61K 2039/545* (2013.01); *A61K 2039/555* (2013.01); *A61K 2039/55588* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 6,797,269 | B2 | 9/2004 | Mosca et al. |
| 9,101,597 | B2 | 8/2015 | Gary et al. |
| 2014/0040801 | A1 | 2/2014 | Patel et al. |
| 2014/0178422 | A1 | 6/2014 | Tomchuck et al. |
| 2015/0343040 | A1 | 12/2015 | Davey et al. |

FOREIGN PATENT DOCUMENTS

| | | |
|---|---|---|
| CN | 104138391 A | 11/2014 |
| EP | 2997971 A2 | 4/2014 |

OTHER PUBLICATIONS

Poole et al, Influenza vaccine for patients with chronic obstructive pulmonary disease (Review), Cochrane Database of Systematic Reviews, 2000, Issue 3, Art No. CD002733 (44 pages) (Year: 2000).*
Grohskopf et al, "Prevention and Control of Influenza with Vaccines: Recommendations of the Advisory Committee on Immunization Practices (ACIP)—United States, 2012-2013 Influenza Season" Morbidity and Mortality Weekly Report, Aug. 17, 2012, vol. 61, No. 32, pp. 613-618. (Year: 2012).*
Hare et al "Comparison of Allogeneic vs Autologous Bone Marrow-derived Mesenchymal Stem Cells Delivered by Transendocardial Injection in Patients with Ischemic Cardiomyopathy" JAMA, 2012, vol. 308, No. 22, pp. 2369-2379. (Year: 2012).*
Wei et al, "The development of a novel cancer immunotherapeutic platform using tumor-targeting mesenchymal stem cells and a protein vaccine", Molecular Therapy, 2011, vol. 19, No. 12, pp. 2249-2257. (Year: 2011).*
Weiss et al "A placebo-controlled, randomized trial of mesenchymal stem cells in COPD", Chest, 2013, vol. 143, Issue 6, pp. 1590-1598. (abstract only) (Year: 2013).*
International Search Report and Written Opinion of the International Searching Authority dated Apr. 20, 2017, in International Application No. PCT/US2017/016200.
Suzanne Tomchuck et al., Mesenchymal Stem Cells as a Novel Vaccine Platform, Frontiers in Cellular and Infection Microbiology, 2:1-8, XP055286040, 2002.
Cao Wei et al., Mesenchymal Stem Cells and Adaptive Immune Responses, Immunology Letters, 168:2:147-153, XP029341675, 2015.
Suzanne Tomchuck et al., Mesenchymal Stem Cells as a Novel Vaccine Platform, Frontiers in Cellular and Infection Microbiology, 2:1-8, XP055286040, 2012.
Gazdic et al, Mesenchymal Stem Cells: A Friend or Foe in Immune-Mediated Diseases, Stem cell Reviews and Reports 11:280-287 (2015).
De Miguel et al., Immunosuppressive Properties of Mesenchymal Stem Cells: Advances and Applications, Current Molecular Medicine 12:574-591 (2012).
Haddad et al., Mechanisms of T-Cell Immunosuppression by Mesenchymal Stromal Cells: What Do We Know So Far? BioMed Research International 216806 (2014).
Ma et al., Immunobiology of mesenchymal stem cells, Cell death and Differentiation 21:216-225 (2014).

(Continued)

*Primary Examiner* — Allison M Fox
(74) *Attorney, Agent, or Firm* — BUCHANAN, INGERSOLL & ROONEY PC

(57) ABSTRACT

The present invention provides a method of enhancing an immune response to a vaccine by administering a vaccine and a population of isolated allogeneic human mesenchymal stem cells. The present invention also provides kits comprising a vaccine in a first container and a population of isolated allogeneic human mesenchymal stem cells in a second container.

22 Claims, 11 Drawing Sheets

(56) References Cited

OTHER PUBLICATIONS

Uccelli et al., Mesenchymal stem cells: a new strategy for immunosuppression? Trends in Immunology 28(5):219-226 (2007).
Zhou et al., Mesenchymal stem cell-based cellular vaccine: An efficient immunotherapeutic strategy for human malignancies, Medical Hypotheses 76:206-207 (2011).
Ghannan S. et al., Immunosuppression by mesenchymal stem cells: mechanisms and clinical applications, Stem Cell Research & Therapy 1:2 (2010).
Hoogduijn M.J. et al., The immunomodulatory properties of mesenchymal stem cells and their use for immunotherapy, International Immunopharmacology 10(12):1496-1500 (2010).
Bernardo M.E. et al., Mesenchymal Stromal Cells: Sensors and Switchers of Inflammation, Cell Stem Cell 13(4):392-402 (2013).
Hubbard, R.E. et al., Frailty, inflammation and the elderly, Biogerontology 11(5):635-641 (2010).
Frasca et al., "Aging, Cytomegalovirus (CMV) and Influenza Vaccine Responses," Human Vaccines & Immunotherapeutics, (Nov. 20, 2015), vol. 12, No. 3, pp. 682-690.
Golpanian et al., "Allogeneic Human Mesenchymal Stem Cell Infusions for Aging Frailty," Journals of Gerontology: Medical Sciences, (2017), vol. 72, No. 11, pp. 1505-1512.
Schulman et al., "Mesenchymal Stem Cell Therapy for Aging Frailty," Frontiers in Nutrition, (Nov. 2018), vol. 5, No. 108, pp. 1-10.
Tompkins et al., "Allogeneic Mesenchymal Stem Cells Ameliorate Aging Frailty: A Phase II Randomized, Double-Blind, Placebo-Controlled Clinical Trial," Journals of Gerontology: Medical Sciences, (2017), vol. 72, No. 11, pp. 1513-1521.
Search Report and Written Opinion dated Mar. 28, 2020, by the Intellectual Property Office of Singapore in corresponding Singapore Patent Application No. 11201806587R. (10 pages).
Aso et al., "Adipose-Derived Mesenchymal Stem Cells Restore Impaired Mucosal Immune Responses in Aged Mice," PLoS One, (Feb. 3, 2016), vol. 11, No. 2, e0148185, pp. 1-15.
Office Action (Notice of Reasons for Rejection) dated Mar. 30, 2021, by the Japanese Patent Office in corresponding Japanese Patent Application No. 2018-541195 and an English Translation of the Office Action. (9 pages).
Kayamuro et al., "Development of Functional Cytokine as New Mucosal Vaccine Adjuvant," Drug Delivery System, (2010), vol. 25, No. 1, (pp. 22-28).
Office Action (Notice of Reasons for Rejection) dated Nov. 9, 2021, by the Japanese Patent Office in corresponding Japanese Patent Application No. 2018-541195 and an English Translation of the Office Action. (7 pages).
Final Office Action (Notice of Reasons for Rejection) dated Sep. 6, 2022, by the Japanese Patent Office in corresponding Japanese Patent Application No. 2018-5411195 and an English Translation of the Office Action.

\* cited by examiner

MESENCHYMAL STEM CELLS AS VACCINE ADJUVANTS AND METHODS FOR USING THE SAME

FIELD OF THE INVENTION

The present invention relates to vaccines and vaccine adjuvants, methods of using the same, and kits comprising the same. In particular, this invention relates to vaccine adjuvants comprising isolated allogeneic human mesenchymal stem cells.

BACKGROUND OF THE INVENTION

Aging Frailty and Inflammaging

Aging frailty poses a very concerning problem for the overall health and well-being of individuals. Aging frailty is a geriatric syndrome characterized by weakness, low physical activity, slowed motor performance, exhaustion, and unintentional weight loss. See Yao, X. et al., *Clinics in Geriatric Medicine* 27(1):79-87 (2011). Furthermore, there are many studies showing a direct correlation between aging frailty and inflammation. See Hubbard, R. E. et al., *Biogerontology* 11(5):635-641 (2010).

Immunosenescence is characterized by a low grade, chronic systemic inflammatory state known as inflammaging. See Franceshi, C. et al., *Annals of the New York Academy of Sciences* 908:244-254 (2000). This heightened inflammatory state or chronic inflammation found in aging and aging frailty leads to immune dysregulation and a complex remodeling of both innate and adaptive immunity. In immunosenescence, the T cell and B cell repertoire is skewed resulting in an increase in $CD8^+$ T effector memory cells re-expressing CD45ra (TEMRA) and in the $CD19^+$ late/exhausted memory B cells, and a decrease in the $CD8^+$ Naïve T cells, and in the switched memory B cells ($CD27^+$). See Blomberg, B. B. et al., *Immunologic Research* 57(1-3):354-360 (2013); Colonna-Romano, G. et al., *Mechanisms of Ageing and Development* 130(10):681-690 (2009); and Koch S. et al., *Immunity & Ageing:* 5:6 (2008). This shift in the T cell and B cell repertoire results in a refractory or less efficient immune status. This deterioration of the immune system causes greater susceptibility to infectious diseases and reduced responses to vaccination. Optimal B cell function is critical for production of effective antibody responses to vaccines and protection from infectious agents. It is well known that age-associated increase in systemic inflammation (TNF-α, IL-6, IL-8, INFγ and CRP) induces impaired B cell function leading to poor antibody responses and decreased vaccine efficacy.

Inflammaging has received considerable attention because it proposes a link between immune changes and a number of diseases and conditions (such as aging frailty) common in old age. Circulating inflammatory mediators such as cytokines and acute phase proteins are markers of the low-grade inflammation observed to increase with aging. These pro-inflammatory cytokines (e.g., TNF-α, IL-6) impair the capacity of B cells to make protective antibodies to exogenous antigens and vaccines. This impaired B cell response is measured by reduced class switch recombination (CSR) which is the ability of immunoglobulins to switch isotype from IgM to a secondary isotype (IgG, IgA, or IgE). Immunoglobulin isotype switching is crucial for a proper immune response as the effector functions differ in each isotype. A key player in CSR and somatic hypermutation (SHM) is the enzyme, activation-induced cytidine deaminase (AID), encoded by the Aicda gene. AID's basic function in CSR and SHM is to initiate breaks in the DNA by converting cytosines to uracils in the switch and variable regions of immunoglobulins. E47, encoded by the Tcfe2a (E2A) gene, is a transcription factor belonging to the class I basic helix loop helix (bHLH) proteins, also known as E proteins. Without E47 expression, the B cell specific transcription factors EBF1 (early B cell factor) and Pax-5 (paired box protein) are not expressed. Both E47 and Pax-5 are key transcription factors in early development for the B cell lineage and mature B cell function. See Hagman J. et al., *Immunity* 27(1):8-10 (2007); Horcher M. et al., *Immunity* 14(6):779-790 (2001); Riley R. L. et al., *Seminars in Immunology* 17(5):330-336 (2005). The Pax-5 gene encodes the B cell lineage specific activator protein (BSAP) that is expressed at all stages of B cell differentiation, but not in terminally differentiated B cells. Pax-5 controls B cell commitment by repressing B lineage inappropriate genes and activating B cell specific genes making Pax-5 the B cell gatekeeper and is exclusively expressed in the B lymphoid lineage from the committed pro-B cell to the mature B cell stage. The B cell specific transcription factor, Pax-5, is not only highly important in early B cell development and B cell lineage commitment, it is also involved in CSR.

It has also been shown in humans that the amount of TNF-α made: (1) depends on the amount of system inflammation and (2) impairs the ability of the same B cells to be stimulated with mitogens or antigens. See Frasca, D. et al., *Journal of Immunology* 188(1):279-286 (2012). Thus, the immune response in subjects suffering from aging frailty is impaired for a number of reasons.

Vaccination in the Elderly

Vaccination against influenza is strongly recommended in individuals over 65 years of age to protect them from infection. Although commercially available vaccines against influenza provide protection and ensure lasting immunological memory in children and adults, they are much less effective in elderly and frail individuals. See Frasca D. et al., *Current Opinion in Immunology* 29:112-118 (2014) and Yao X. et al., *Vaccine* 29(31):5015-5021 (2011). Despite receiving the influenza vaccine routinely, elderly individuals are at higher risk of infection with influenza leading to secondary complications, hospitalization, physical debilitation, ultimately death. See Gross, P. et al., *Annals of Internal Medicine* 123(7):518-527 (1995); Simonsen L. et al., *The Journal of Infectious Diseases* 178(1):53-60 (1998); and Vu T. et al., *Vaccine* 20(13-14):1831-1836 (2002). Influenza vaccines also prevent other complications that arise from influenza infection (e.g., pneumonia) in most elderly individuals, reducing the rate of hospitalization to some extent. Nichol K. L. et al., *The New England Journal of Medicine* 331(12):778-784 (1994). However, the rate of hospitalization due to influenza-related disease is still very high. See Thompson, W. W. et al., *JAMA* 292(11):1333-1340 (2004). Thus, there remains a need for enhancing the immune response of a vaccine in the elderly.

Previous published results have shown that the specific response of B cells to the influenza vaccine in vitro (measured by AID), and the in vivo serum response (measured by HAI assay and ELISA), decrease with aging and are significantly correlated. See Frasca, D. et al., *Vaccine* 28(51):8077-8084 (2010). It was also found that the percentage of switched memory B cells and CpG-induced AID, both measured before vaccination (t0), are decreased with aging and are significantly correlated with the in vivo response. Thus, these markers are predictive of the in vivo response.

Mesenchymal Stem Cells

Mesenchymal stem cells are multipotent cells able to migrate to sites of injury, while also being immunoprivileged by not detectably expressing major histocompatibility complex class II (MHC-II) molecules, and expressing MHC-I molecules at low levels. See Le Blanc, K. et al., *Lancet* 371(9624):1579-1586 (2008) and Klyushnenkova E. et al., *J. Biomed. Sci.* 12(1):47-57 (2005). As such, allogeneic mesenchymal stem cells hold great promise for therapeutic and regenerative medicine, and have been repeatedly shown to have a high safety and efficacy profile in clinical trials for multiple disease processes. See Hare, J. M. et al., *Journal of the American College of Cardiology* 54(24): 2277-2286 (2009); Hare, J. M. et al., *Tex. Heart Inst. J.* 36(2):145-147 (2009); and Lalu, M. M. et al., *PloS One* 7(10):e47559 (2012). They have also been shown to not undergo malignant transformation after transplantation into patients. See Togel F. et al., *American Journal of Physiology Renal Physiology* 289(1):F31-F42 (2005). Treatment with mesenchymal stem cells has been shown to ameliorate severe graft-versus-host disease, protect against ischemic acute renal failure, contribute to pancreatic islet and renal glomerular repair in diabetes, reverse fuliminant hepatic failure, regenerate damaged lung tissue, attenuate sepsis, and reverse remodeling and improve cardiac function after myocardial infarction. See Le Blanc K. et al., *Lancet* 371(9624): 1579-1586 (2008); Hare, J. M. et al., *Journal of the American College of Cardiology* 54(24):2277-2286 (2009); Togel F. et al., *American Journal of Physiology Renal Physiology* 289(1):F31-F42 (2005); Lee R. H. et al., *PNAS* 103(46): 17438-17442 (2006); Parekkadan, B. et al., *PloS One* 2(9): e941 (2007); Ishizawa K. et al., *FEBS Letters* 556(1-3):249-252 (2004); Nemeth K. et al., *Nature Medicine* 15(1):42-49 (2009); Iso Y. et al., *Biochem. Biophys. Res. Comm.* 354(3): 700-706 (2007); Schuleri K. H. et al., *Eur. Hearth J.* 30(22):2722-2732 (2009); and Heldman A. W. et al., *JAMA* 311(1):62-73 (2014). Furthermore, mesenchymal stem cells are also a potential source of multiple cell types for use in tissue engineering. See Gong Z. et al., *Methods in Mol. Bio.* 698:279-294 (2011); Price, A. P. et al., *Tissue Engineering Part A* 16(8):2581-2591 (2010); and Togel F. et al., *Organogenesis* 7(2):96-100 (2011).

Mesenchymal stem cells have immuno-modulatory capacity. They control inflammation and the cytokine production of lymphocytes and myeloid-derived immune cells without evidence of immunosuppressive toxicity and are hypo-immunogenic. See Bernardo M. E. et al., *Cell Stem Cell* 13(4):392-402 (2013).

Mesenchymal stem cells also have the capacity to differentiate not only into cells of mesodermal origin, but into cells of endodermal and ectodermal origin. See Le Blanc K. et al., *Exp. Hematol.* 31(10):890-896 (2003). For example, in vitro, mesenchymal stem cells cultured in airway growth media differentiate to express lung-specific epithelial markers, e.g., surfactant protein-C, Clara cell secretory protein, and thyroid transcription factor-1. See Jiang Y. et al., *Nature* 418(6893):41-49 (2002) and Kotton D. N. et al., *Development* 128(24):5181-5188 (2001).

In vivo studies have shown that human mesenchymal stem cells undergo site-specific differentiation into various cell types, including myocytes and cardiomyocytes, when transplanted into fetal sheep. See Airey J. A. et al., *Circulation* 109(11):1401-1407 (2004). These mesenchymal stem cells can persist for as long as 13 months in multiple tissues after transplantation in non-immunosuppressed immunocompetent hosts. Other in vivo studies using rodents, dogs, goats, and baboons similarly demonstrate that human mesenchymal stem cells xenografts do not evoke lymphocyte proliferation or systemic allo-antibody production in the recipient. See Klyushnenkova E. et al., *J. Biomed. Sci.* 12(1):47-57 (2005); Aggarwal S. et al., *Blood* 105(4):1815-22 (2005); Augello A. et al., *Arthritis and Rheumatism* 56(4):1175-86 (2007); Bartholomew A. et al., *Exp Hematol.* 30(1):42-48. (2002); Dokic J. et al., *European Journal of Immunology* 43(7):1862-72 (2013); Gerdoni E. et al., *Annals of Neurology* 61(3):219-227 (2007); Lee S. H. et al., *Respiratory Research* 11:16 (2010); Urban V. S. et al., *Stem Cells* 26(1):244-253 (2008); Yang H. et al., *PloS One* 8(7):e69129 (2013); Zappia E. et al., *Blood* 106(5):1755-1761 (2005); Bonfield T. L. et al., *American Journal of Physiology Lung Cellular and Molecular Physiology* 299(6):L760-70 (2010); Glenn J. D. et al., *World Journal of Stem Cells.* 6(5):526-39 (2014); Guo K. et al., *Frontiers in Cell and Developmental Biology* 2:8 (2014); Puissant B. et al., *British Journal of Haematology* 129(1):118-129 (2005); and Sun L. et al., *Stem Cells* 27(6):1421-32 (2009). Taken as a whole, these repeated finding of allogeneic safety and efficacy solidify the notion for using mesenchymal stem cells as an allograft for successful tissue regeneration.

However, despite being a safe therapeutic agent, mesenchymal stem cells are reported in the literature to exert a suppressive effect on antibody production as well as proliferation and maturation of B cells. See Uccelli, A. et al., *Trends in Immunology* 28(5):219-226 (2007). Mesenchymal stem cells are also reported to inhibit the generation and function of antigen presenting cells. See Hoogduijn M. J. et al., *Int. Immunopharmacology* 10(12):1496-1500 (2010). Finally, mesenchymal stem cells are reported to suppress $CD4^+$ and $CD8^+$ T cell proliferation. See Ghannam S. et al., *Stem Cell Res. & Ther.* 1:2 (2010).

SUMMARY

Surprisingly, despite the reports of mesenchymal stem cells having a suppressive effect on aspects of the immune system, the present inventors discovered a method of enhancing a subject's immune response to a vaccine or of inducing an immune response in a non-responding subject, comprising administering to the subject concurrently or sequentially the vaccine and an adjuvant in immunoprotective amounts, wherein the adjuvant is a population of isolated allogeneic human mesenchymal stem cells, and kits and uses related thereto.

In one embodiment of the invention, the subject is a human. In another embodiment of the invention, the subject is a human who exhibits symptoms of aging frailty. In another embodiment of the invention, the subject is a human who exhibits inflammaging.

In one embodiment of the invention, the mesenchymal stem cells are bone marrow-derived mesenchymal stem cells. In one embodiment of the invention, the mesenchymal stem cells do not express STRO-1. In another embodiment of the invention, the mesenchymal stem cells do not express CD45. In another embodiment of the invention, the mesenchymal stem cells do not express fibroblast surface markers or have a fibroblast morphology. In another embodiment of the invention, the mesenchymal stem cells are not genetically manipulated.

In one embodiment of the invention, the vaccine is monovalent. In another embodiment of the invention, the vaccine is multivalent. In one embodiment of the invention, the vaccine comprises one or more inactivated viruses. In a further embodiment, the one or more inactivated viruses are selected from the group consisting of adenoviruses, picornaviruses, papillomaviruses, polyomaviruses, hepadnaviruses, parvoviruses, pox viruses, Epstein-Barr virus, cytomegalovirus (CMV), herpes viruses, roseolovirus, varicella zoster virus, filoviruses, paramyxoviruses, orthomyxoviruses, rhabdoviruses, arenaviruses, coronaviruses, human enteroviruses, hepatitis A virus, human rhinoviruses, polio virus, retroviruses, rotaviruses, flaviviruses, hepaciviruses, togaviruses, and rubella virus. In a further embodiment, the vaccine comprises an inactivated orthomyxovirus. In a further embodiment, the vaccine comprises an inactivated influenza virus. In one embodiment of the invention, the vaccine comprises one or more live, attenuated viruses. In a further embodiment, the one or more attenuated viruses are selected from the group consisting of adenoviruses, picornaviruses, papillomaviruses, polyomaviruses, hepadnaviruses, parvoviruses, pox viruses, Epstein-Barr virus, cytomegalovirus (CMV), herpes viruses, roseolovirus, varicella zoster virus, filoviruses, paramyxoviruses, orthomyxoviruses, rhabdoviruses, arenaviruses, coronaviruses, human enteroviruses, hepatitis A virus, human rhinoviruses, polio virus, retroviruses, rotaviruses, flaviviruses, hepaciviruses, togaviruses, and rubella virus.

In one embodiment of the invention, the adjuvant is administered before the vaccine. In a further embodiment, the adjuvant is administered at least 1 week before the vaccine is administered. In a further embodiment, the adjuvant is administered at least 2 weeks before the vaccine is administered. In a further embodiment, the adjuvant is administered at least 3 weeks before the vaccine is administered. In a further embodiment, the adjuvant is administered at least 4 weeks before the vaccine is administered. In another embodiment of the invention, the adjuvant is administered at least yearly for long-term enhancement of vaccine response.

In one embodiment of the invention, the adjuvant and the vaccine are administered parenterally. In one embodiment, the adjuvant is administered systemically. In one embodiment of the invention, the adjuvant is administered by infusion or direct injection. In one embodiment of the invention, the adjuvant is administered intravenously, intraarterially, or intraperitoneally. In a further embodiment, the adjuvant is administered intravenously. In one embodiment of the invention, the vaccine is administered intramuscularly, intravenously, intraarterially, intraperitoneally, subcutaneously, intradermally, orally, or intranasally. In a further embodiment, the vaccine is administered intramuscularly.

In one embodiment of the invention, the adjuvant is administered at a dose of about $20 \times 10^6$ mesenchymal stem cells. In another embodiment of the invention, the adjuvant is administered at a dose of about $100 \times 10^6$ mesenchymal stem cells. In another embodiment of the invention, the adjuvant is administered at a dose of about $200 \times 10^6$ mesenchymal stem cells.

In one embodiment of the invention, the mesenchymal stem cells are obtained from a human donor and a step of MHC matching of the human donor to the subject is not employed prior to the administration of the vaccine and adjuvant to the subject.

In one embodiment of the invention, as a result of the disclosed methods of enhancing a subject's immune response to a vaccine or of inducing an immune response in a non-responding subject, comprising administering to the subject concurrently or sequentially the vaccine and an adjuvant in immunoprotective amounts, wherein the adjuvant is a population of isolated allogeneic human mesenchymal stem cells, the intracellular TNF-α expression in the B cells of the subject decreases by at least two-fold as compared to the TNF-α expression levels in B cells of the subject prior to administration of the adjuvant. In another embodiment of the invention, the CD4$^+$:CD8$^+$ T cell ratio in the subject increases by at least two-fold as compared to the CD4$^+$:CD8$^+$ T cell ratio in the subject prior to administration of the adjuvant. In another embodiment of the invention, the number of switched memory B cells in the subject increases by at least two-fold as compared to the number of switched memory B cells in the subject prior to administration of the adjuvant. In another embodiment of the invention, the number of exhausted B cells in the subject decreases by at least two-fold as compared to the number of exhausted B cells in the subject prior to administration of the adjuvant. In another embodiment, the invention concerns a method of inducing an immune response in a subject comprising administering to the subject concurrently or sequentially a vaccine and an adjuvant in immunoprotective amounts, wherein the adjuvant is a population of isolated allogeneic human mesenchymal stem cells, and further wherein the intracellular TNF-α expression in B cells of the subject decreases by at least two-fold as compared to the TNF-α expression levels in B cells of the subject prior to administration of the adjuvant. The invention also concerns a method of inducing an immune response in a subject comprising administering to the subject concurrently or sequentially a vaccine and an adjuvant in immunoprotective amounts, wherein the adjuvant is a population of isolated allogeneic human mesenchymal stem cells, and further wherein the CD4+:CD8+ T cell ratio in the subject increases by at least two-fold as compared to the CD4+:CD8+ T cell ratio in the subject prior to administration of the adjuvant. The invention further concerns a method of inducing an immune response in a subject comprising administering to the subject concurrently or sequentially a vaccine and an adjuvant in immuoprotective amounts, wherein the adjuvant is a population of isolated allogeneic human mesenchymal stem cells, and further, wherein the number of switched memory B cells in the subject increases by at least two-fold as compared to the number of switched memory B cells in the subject prior to administration of the adjuvant. The invention still further concerns a method of inducing an immune response in a subject comprising administering to the subject concurrently or sequentially a vaccine and an adjuvant in immuoprotective amounts, wherein the adjuvant is a population of isolated allogeneic human mesenchymal stem cells, and further wherein the number of exhausted B cells in the subject decreases by at least two-fold as compared to the number of exhausted B cells in the subject prior to administration of the adjuvant.

In another aspect, the invention relates to a kit having at least two containers, comprising: a vaccine in a first container and an adjuvant in a second container, wherein the adjuvant is a population of isolated allogeneic human mesenchymal stem cells. In one embodiment of the invention, the mesenchymal stem cells of the kit are cryopreserved. In one embodiment of the invention, the kit further comprises dilution buffer in a third container. The vaccines and the mesenchymal stem cells present in the kit may be any of the vaccines or allogeneic human mesenchymal stem cells disclosed herein.

BRIEF DESCRIPTION OF THE DRAWING FIGURES

FIG. 1A shows RT-PCR for E47 and GAPDH from five subjects. FIG. 1B shows the densitometry analyses of CT's normalized to GAPDH.

FIG. 2 shows AID mRNA expression correlated to E47 expression. Reproduced from FIG. 3 of Frasca, D. et al., *J. Immunol.* 180(8):5283-5290 (2008).

FIGS. 5A-5D show T cell concentrations as measured by flow cytometry. FIGS. 5A-5D show that there is no T cell activation (rejection) induced by the allogeneic mesenchymal stem cells at any dose. CD69 is an early marker of T cell activation. CD25 is a late/chronic marker of T cell activation.

Figure 6:
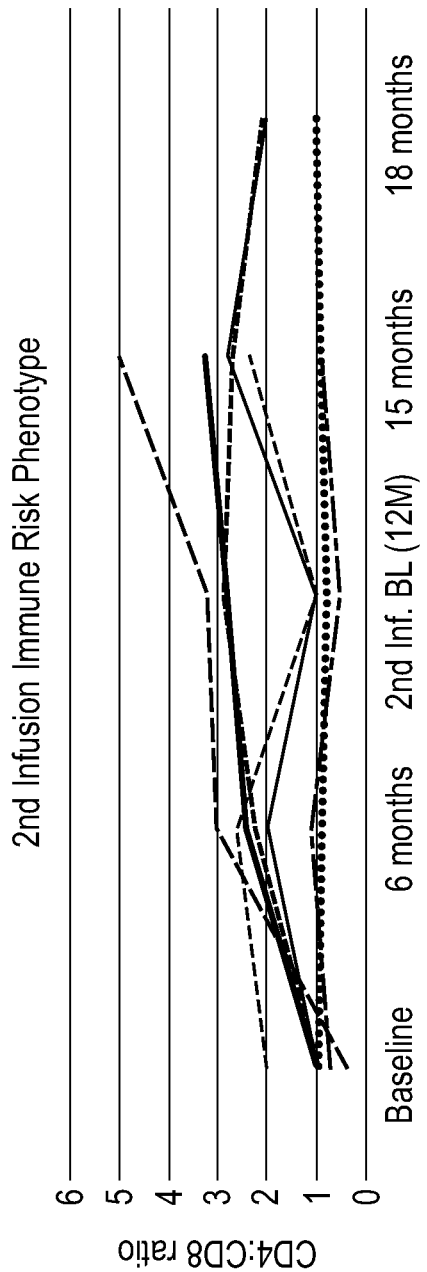

FIG. 6 shows CD4$^+$:CD8$^+$ T cell ratios, calculated from flow cytometry measurements. An improvement in the CD4$^+$:CD8$^+$ T cell ratio (Immune Risk Phenotype) was observed in subjects who received a second mesenchymal stem cell infusion one year after their first mesenchymal stem cell infusion.

Figure 7A:
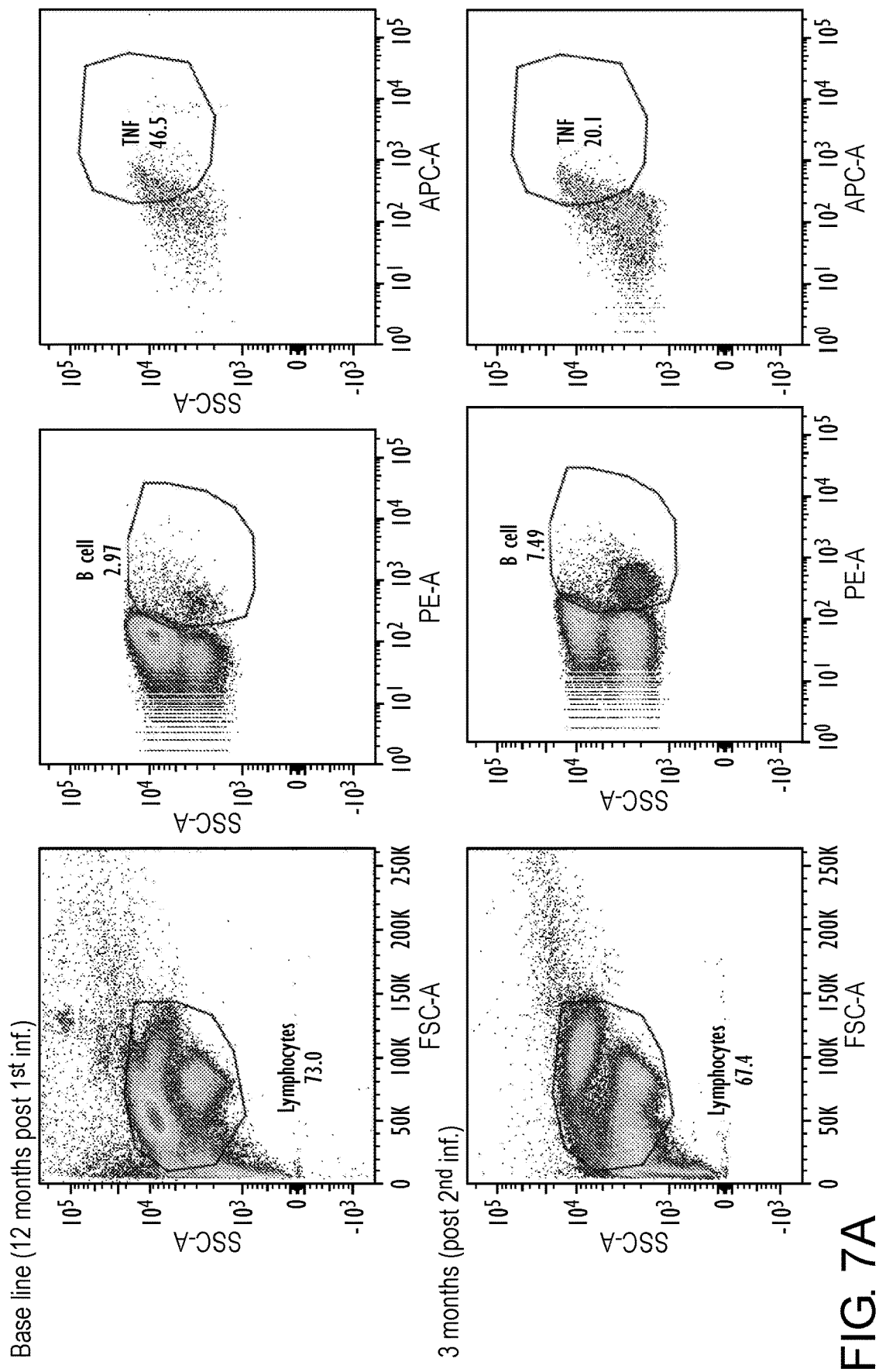
Figure 7B:
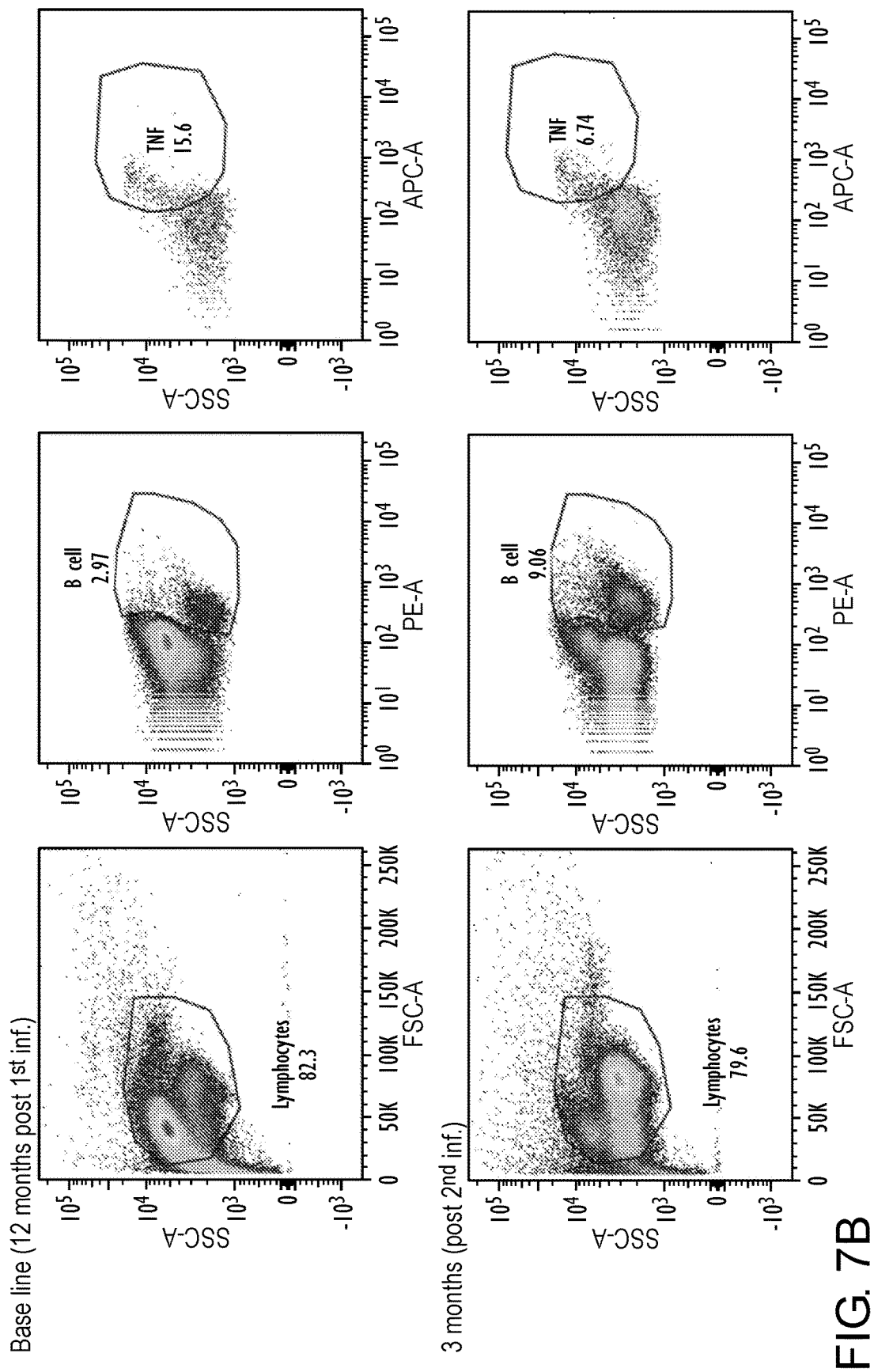

FIGS. 7A and 7B show downregulation of intracellular TNF-α in B cells by flow cytometry after mesenchymal stem cell infusion. "Base line" refers to flow cytometry measurements taken at baseline. "3 months" refers to flow cytometry measurements taken 3 months after subjects received a second mesenchymal stem cell infusion one year after their first mesenchymal stem cell infusion. "FSC-A" is forward-scattered light and is proportional to cell-surface area or size. "SSC-A" is side-scattered light and is proportional to cell granularity or internal complexity. Thus, correlated measurements of FSC-A and SSC-A allow for differentiation of cell types in a heterogeneous population (e.g., lymphocytes). "PE-A" is measurement of phycoerythrin, a fluorochrome. "APC-A" is measurement of allphycocyanin, another fluorochrome. FIG. 7A shows the flow cytometry measurements from one CRATUS subject. FIG. 7B shows the flow cytometry measurements from a second CRATUS subject.

DETAILED DESCRIPTION

In certain embodiments, the present invention is directed to methods of improving the immune response to vaccines in elderly patients. The examples demonstrate that in vivo administration of isolated allogeneic human mesenchymal stem cells result in an increase in the percentage of switched memory B cells and a decrease in exhausted B cells in subjects. The examples also demonstrate that in vivo administration of isolated allogeneic human mesenchymal stem cells results in an improvement in the CD4$^+$:CD8$^+$ T cell ratio in subjects. Also, as shown in the examples, intracellular TNF-α is reduced in subjects having received infusions of allogeneic human mesenchymal stem cells. From these unexpected results, the present inventors determined that isolated allogeneic human mesenchymal stem cells are effective at reducing inflammaging, a prevalent feature in aging frailty. And because isolated allogeneic human mesenchymal stem cells were shown to reduce inflammaging, these mesenchymal stem cells enhance the immune response to vaccination.

Definitions

Embodiments may be practiced without the theoretical aspects presented. Moreover, the theoretical aspects are presented with the understanding that the embodiments are not bound by any theory presented.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of ±10% of the referenced value.

Dosage, Duration and Subjects

"Immunoprotective amount" means an amount that stimulates a T cell dependent (TD) immune response. Such a response is characterized by the ability to elicit significant levels of IgG and opsonic activity. An immunological memory is developed to the immunogenic antigen such that the antibodies produced ameliorate the infection and disease condition mediated by the pathogen and/or prevent infection by the pathogen. The dosage and number of doses (e.g., single or multiple dose) administered to the subject will vary depending upon a variety of factors, including the route of administration, patient conditions and characteristics (sex, age, body weight, health, size), extent of symptoms, concurrent treatments, frequency of treatment and the effect desired, and the like.

As used herein, the "immunoprotective amount" of a vaccine and adjuvant is determined based on the effect of the combination of the adjuvant and vaccine. For example, if the adjuvant is shown to enhance the immune response of a vaccine significantly, the amount of vaccine needed is less than if the adjuvant enhances the immune response of the vaccine less. Useful amounts of adjuvant and vaccine can be determined by a person of skill in the field using known dosage development techniques. In one embodiment, the invention comprises a method of enhancing a subject's immune response to a vaccine or inducing an immune response in a non-responding subject, comprising administering to the subject concurrently or sequentially the vaccine and an adjuvant in immunoprotective amounts, wherein the adjuvant is a population of isolated allogeneic human mesenchymal stem cells, and further wherein the amount of vaccine required for immunoprotective effect is less than half that required for immunoprotective effect in the absence of use of the adjuvant. In other embodiments, the amount of vaccine required for immunoprotective effect is less than 0.1%, less than 0.5%, less than 1.0%, less than 10%, less than 20%, or less than 30% that required for immunoprotective effect in the absence of use of the adjuvant.

In one embodiment of the invention, the adjuvant is administered concurrently with the vaccine. In another embodiment of the invention, the adjuvant is administered sequentially with the vaccine. In a further embodiment, the adjuvant is administered at least 1 week before the vaccine is administered. In a further embodiment, the adjuvant is administered as least 2 weeks before the vaccine is administered. In a further embodiment, the adjuvant is administered at least 3 weeks before the vaccine is administered. In a further embodiment, the adjuvant is administered at least 4 weeks before the vaccine is administered. In other embodiments, the adjuvant is administered from about 1-8 weeks, 1-12 weeks, 1-36 weeks, 2-8 weeks, 2-12 weeks, 2-26 weeks, 2-36 weeks, 2-48 weeks, 3-4 weeks, 3-12 weeks, 3-8 weeks, 3-26 weeks, 3-36 weeks, 3-48 weeks, or 4-12 weeks prior to administration of the vaccine. In other embodiments, the adjuvant is administered about 1, 2, 3, 4, 5, 6, 7, 8, 9, or 10 months prior to administration of the vaccine, or from 1-2 months, 1-3 months, 1-4 months, 1-5 months, 1-6 months, 2-3 months, 2-4 months, 2-6 months, or 3-6 months prior to administration of the vaccine. In certain embodiments of the invention, the adjuvant is administered at least yearly for long-term enhancement of the subject's vaccine response. This disclosure also concerns methods in which the vaccine is administered in advance of the adjuvant, such as, without limitation, from about 1-8 weeks, 1-12 weeks, 1-36 weeks, 2-8 weeks, 2-12 weeks, 3-4 weeks, 3-12 weeks, 3-8 weeks, or 4-12 weeks prior to administration of the adjuvant.

In another embodiment of the invention, the administration of the adjuvant and vaccine is repeated, such as at least 4, 5, 6, 7, 8, 9, 10, 11, 12, 13, 14, 15, 16, 17, or 18 months after the first administration of the vaccine, or repeated between 2-4, 2-6, 2-8, 2-10, 3-4, 3-6, 3-8, 3-10, 4-6, 4-8, 4-10, 6-8, 6-10, 6-12, or 12-18 months after the first administration of the vaccine. Repeated administration of the "the vaccine" includes without limitation an administration of a vaccine for an influenza virus that is then followed by a vaccine for influenza virus that is not identical to the first vaccine but is recognized to provide vaccination for the type of influenza virus in its prevalent serotypes at the time of the second or repeated administration. In other embodiments, the administration of adjuvant and vaccine, concurrently or sequentially, is repeated three times, four times, five times, six times, or 5-10 times. For example, without limitation, the invention includes administering the adjuvant at day 0, then at day 7 administering the vaccine, then at day 180 administering the adjuvant, and then at day 187 administering the vaccine. In certain embodiments the actual vaccine contents may differ during this repeated therapy, however, the vaccine administered at each point in the repeated therapy would be directed against the same class of pathogen.

In one embodiment of the invention, the adjuvant is administered at a dose of about $1 \times 10^6$, $2 \times 10^6$, $5 \times 10^6$, $10 \times 10^6$, $20 \times 10^6$, $30 \times 10^6$, $40 \times 10^6$, $50 \times 10^6$, $60 \times 10^6$, $70 \times 10^6$, $80 \times 10^6$, $90 \times 10^6$, $100 \times 10^6$, $110 \times 10^6$, $120 \times 10^6$, $130 \times 10^6$, $140 \times 10^6$, $150 \times 10^6$, $160 \times 10^6$, $170 \times 10^6$, $180 \times 10^6$, $190 \times 10^6$, $200 \times 10^6$, $300 \times 10^6$, $400 \times 10^6$, $500 \times 10^6$, or $10 \times 10^7$ mesenchymal stem cells. In a further embodiment, the adjuvant is administered at a dose of about $20 \times 10^6$ mesenchymal stem cells. In a further embodiment, the adjuvant is administered at a dose of about $100 \times 10^6$ mesenchymal stem cells. In yet a further embodiment, the adjuvant is administered at a dose of about $200 \times 10^6$ mesenchymal stem cells. In further embodiments, the adjuvant is administered at a dose of from about $1-400 \times 10^6$, $10-400 \times 10^6$, $100-400 \times 10^6$, $20-200 \times 10^6$, $20-400 \times 10^6$, $0.1-5 \times 10^6$, $0.1-10 \times 10^6$, $0.1-100 \times 10^6$, $1-50 \times 10^6$, $1-100 \times 10^6$, $0.01-10 \times 10^6$ or $0.01-100 \times 10^6$ mesenchymal stem cells.

In some embodiments, the immunoprotective amount of adjuvant is sufficient to increase the ratio of $CD4^+$:$CD8^+$ T cells in a subject, such as to increase the ratio of $CD4^+$:$CD8^+$ T cells by at least two-, three, four-, five-, or six-fold as compared to the ratio prior to administration of the adjuvant. In some embodiments, the immunoprotective amount of adjuvant is sufficient to increase the number of switched memory B cells in a subject, such as to increase the number of switched memory B cells by at least two-, three-, four-, or five-fold as compared to the number prior to administration of the adjuvant. In some embodiments, the immunoprotective amount is sufficient to decrease the intracellular TNF-α expression in the B cells of a subject, such as to decrease the intracellular TNF-α amounts in B cells by at least two-, three-, four-, five-, or six-fold as compared to the amounts in B cells prior to administration of the adjuvant. In some embodiments, the immunoprotective amount is sufficient to upregulate activation-induced cytidine deaminase (AID) in a subject. In some embodiments, the immunoprotective amount is sufficient to decrease the number of exhausted B cells in a subject, such as to decrease the number of exhausted B cells by at least two- or three-fold as compared to the number prior to administration of the adjuvant.

In a further embodiment, the use of an adjuvant allows for administration of lower levels of vaccine than those advised in the absence of adjuvant for the patient population at issue and still obtains an immune response. For example, current recommendations call for a single 0.5 mL dose intramuscular injection of the Fluzone High-Dose vaccine (Sanofi Pasteur) for patients ≥65 years of age. In the methods of the present invention, the amount of Fluzone vaccine may be reduced to less than that, such as 0.3 or 0.2 mL for a patient ≥65 years of age.

"Administering" a composition may be accomplished by oral administration, injection, infusion, parenteral, intravenous, mucosal, sublingual, intramuscular, intradermal, intranasal, intraperitoneal, intraarterial, subcutaneous absorption or by any method in combination with other known techniques. In one embodiment of the invention, the adjuvant is administered systemically. In another embodiment of the invention, the adjuvant is administered by infusion or direct injection. In another embodiment of the invention, the adjuvant is administered intravenously, intraarterially, or intraperitoneally. In a further embodiment, the adjuvant is administered intravenously. In one embodiment of the invention, the vaccine is administered intramuscularly, intravenously, intraarteerially, intraperitoneally, subcutaneously, intradermally, orally, or intranasally. In a further embodiment, the vaccine is administered intramuscularly.

The term "subject" as used herein includes, but is not limited to, humans and non-human vertebrates such as wild, domestic, and farm animals. In some embodiments, the term refers to non-human animals, such as dogs, cats, birds, mice, rats, rabbits, guinea pigs, hamsters, gerbils, goats, sheep, bovines, horses, camels, non-human primates, etc. In some embodiments, the term refers to humans, such as elderly humans ≥65 years of age, or elderly humans 60-95 years of age. In some embodiments, the human subject exhibits symptoms of aging frailty. In some embodiments, the human subject exhibits inflammaging.

In one embodiment of the invention, the subject is a non-responder. It is known that, when a population of individuals is vaccinated against a disease, a number of them do not "respond" to the vaccination, that is to say that their immune system does not appear to react to the antigen administered. This problem is substantial to a greater or lesser degree depending on the diseases and the populations involved, but vaccine manufacturers are still trying to reduce, for each of the vaccines which they make available to doctors, the number of subjects likely to be "non-responders." This problem is considered particularly important for vaccines comprising purified antigens such as subunit vaccines produced by genetic engineering.

The term "allogeneic" refers to a cell that is of the same animal species but genetically different in one or more genetic loci as the animal that becomes the "recipient host." This usually applies to cells transplanted from one animal to another non-identical animal of the same species.

As used herein, the phrase "in need thereof" means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, or condition is prevalent.

Cells are referred to herein as being positive or negative for certain markers. For example, a cell can be negative for CD45, which can also be referred to as CD45$^-$. The superscript notation "−" refers to a cell that is negative for the marker linked to the superscript. In contrast a marker with the "+" refers to a cell that is positive for that marker. For example, a cell that is referenced as "CD8$^+$" is positive for CD8. A "+" can also be used to reference the marker as positive. A "−" can also be used to reference the marker as negative.

As used herein, the term "stem cell" refers to a cell from the embryo, fetus, or adult that has, under certain conditions, the ability to reproduce itself for long periods or, in the case of adult stem cells, throughout the life of the organism. It also can give rise to specialized cells that make up the tissues and organs of the body.

Mesenchymal stem cells are the formative pluripotent blast cells found inter alia in bone marrow, blood, dermis, and periosteum that are capable of differentiating into any kind of the specific types of mesenchymal or connective tissues (i.e., the tissues of the body that support the specialized elements; particularly adipose, osseous, cartilaginous, elastic, and fibrous connective tissues) depending upon various influences from bioactive factors, such as cytokines.

Certain methods of isolating and/or purifying mesenchymal stem cells have been described herein and are known in the art. In some embodiments, mesenchymal stem cells are isolated from bone marrow of adult humans. In some embodiments, the cells are passed through a density gradient to eliminate undesired cell types. The cells can be plated and cultured in appropriate media. In some embodiments, the cells are cultured for at least one day or about three to about seven days, and removing non-adherent cells. The adherent cells can then be plated and expanded.

Other methods for isolating and culturing stem cells are also known. Placenta is an excellent readily available source for mesenchymal stem cells. Moreover, mesenchymal stem cells can be derivable from adipose tissue and bone marrow stromal cells are speculated to be present in other tissues. While there are dramatic qualitative and quantitative differences in the organs from which adult stem cells can be derived, the initial differences between the cells may be relatively superficial and balanced by the similar range of plasticity they exhibit.

Homogeneous human mesenchymal stem cell compositions are provided which serve as the progenitors for all mesenchymal cell lineages. Mesenchymal stem cells are identified by specific cell surface markers which are identified with unique monoclonal antibodies. The homogeneous mesenchymal stem cell compositions are obtained by positive selection of adherent marrow or periosteal cells which are free of markers associated with either hematopoietic or differentiated mesenchymal cells. These isolated mesenchymal cell populations display epitopic characteristics associated with only mesenchymal stem cells, have the ability to regenerate in culture without differentiating, and have the ability to differentiate into specific mesenchymal lineages when either induced in vitro or placed in vivo at a site of inflammation.

In order to obtain the human mesenchymal stem cells for the compositions, methods, and kits disclosed herein, pluripotent mesenchymal stem cells are separated from other cells in the bone marrow or other mesenchymal stem cell source. Bone marrow cells may be obtained from iliac crest, femora, tibiae, spine, rib, or other medullary spaces. Other spaces of human mesenchymal stem cells include embryonic yolk sac, placenta, umbilical cord, fetal and adolescent skin, and blood.

In some embodiments, the human mesenchymal stem cells are identified by the absence of markers. For example, human mesenchymal stem cells useful in the invention include those that are negative for STRO-1 and/or negative for CD45. Similarly, human mesenchymal stem cells useful in the invention include those that do not express fibroblast surface markers or have a fibroblast morphology.

Methods of Enhancing Immune Responses and Kits Therefor

As discussed above, the present invention is directed to a method of enhancing a subject's immune response to a vaccine or inducing an immune response in a non-responding subject, comprising administering to the subject concurrently or sequentially the vaccine and an adjuvant in immunoprotective amounts, wherein the adjuvant comprises a population of isolated allogeneic human mesenchymal stem cells, and kits associated with such methods. In some embodiments of the invention, the mesenchymal stem cells are not genetically manipulated. In some embodiments of the invention, the mesenchymal stem cells are obtained from a human donor and wherein a step of MHC matching of the human donor to the subject is not employed prior to the administration of the vaccine and adjuvant to the subject.

In one embodiment of the invention, the vaccine is monovalent. In another embodiment of the invention, the vaccine is multivalent.

In one embodiment of the invention, the vaccine comprises one or more inactivated viruses. In a further embodiment, the one or more inactivated viruses are selected from the group consisting of adenoviruses, picornaviruses, papillomaviruses, polyomaviruses, hepadnaviruses, parvoviruses, pox viruses, Epstein-Barr virus, cytomegalovirus (CMV), herpes viruses, roseolovirus, varicella zoster virus, filoviruses, paramyxoviruses, orthomyxoviruses, rhabdoviruses, arenaviruses, coronaviruses, human enteroviruses, hepatitis A virus, human rhinoviruses, polio virus, retroviruses, rotaviruses, flaviviruses, hepaciviruses, togaviruses, and rubella virus. In a further embodiment, the vaccine comprises an inactivated orthomyxovirus. In a further embodiment, the vaccine comprises an inactivated influenza virus.

In one embodiment of the invention, the vaccine comprises one or more live, attenuated viruses. In a further embodiment, the one or more attenuated viruses are selected from the group consisting of adenoviruses, picornaviruses, papillomaviruses, polyomaviruses, hepadnaviruses, parvoviruses, pox viruses, Epstein-Barr virus, cytomegalovirus (CMV), herpes viruses, roseolovirus, varicella zoster virus, filoviruses, paramyxoviruses, orthomyxoviruses, rhabdoviruses, arenaviruses, coronaviruses, human enteroviruses, hepatitis A virus, human rhinoviruses, polio virus, retroviruses, rotaviruses, flaviviruses, hepaciviruses, togaviruses, and rubella virus.

In another embodiment of the invention, the vaccine comprises an antigen from a bacterial pathogen. In a further embodiment, the bacterial pathogen is selected from the group consisting of: *Bacillus, Bartonella, Bordetella, Borrelia, Brucella, Burkholderia, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio*, and *Yersinia*.

In another embodiment of the invention, the vaccine comprises an antigen from a parasitic pathogen. In a further embodiment, the parasitic pathogen is selected from the group consisting of: *Acanthamoeba, Anisakis, Ascaris lumbricoides, Balantidium coli, Cestoda*, Chiggers, *Cochliomyia hominivorax, Entamoeba histolytica, Fasciola hepatica, Giardia lamblia*, Hookworm, *Leishmania, Linguatula serrate*, Liver fluke, Loa boa, *Paragonimus*, Pinworm, *Plasmodium falciparum, Schistosoma, Strongyloides stercoralis*, Tapeworm, *Toxoplasma gondii, Trypanasoma*, Whipworm, and *Wuchereria bancrofti*.

In another embodiment of the invention, the vaccine comprises one or more antigenic polypeptides selected from the group consisting of influenza hemagglutinin 1 (HA1), hemagglutinin 2 (HA2), influenza neuraminidase (NA), Lassa virus (LASV) glycoprotein 1 (gp1), LASV glycoprotein 2 (gp2), LASV nucleocapsid-associated protein (NP), LASV L protein, LASV Z protein, SARS virus S protein, Ebola virus GP2, measles virus fusion 1 (F1) protein, HIV-1 transmembrane (TM) protein, HIV-1 glycoprotein 41 (gp41), HIV-1 glycoprotein 120 (gp120), hepatitis C virus (HCV) envelope glycoprotein 1 (E1), HCV envelope glycoprotein 2 (E2), HCV nucleocapsid protein (p22), West Nile virus (WNV) envelope glycoprotein (E), Japanese encephalitis virus (JEV) envelope glycoprotein (E), yellow fever virus (YFV) envelope glycoprotein (E), tick-borne encephalitis virus (TBEV) envelope glycoprotein (E), hepatitis G virus (HGV) envelope glycoprotein 1 (E1), respiratory syncytial virus (RSV) fusion (F) protein, herpes simplex virus1 (HSV-1) gD protein, HSV-1 gG protein, HSV-2 gD protein, HSV-2 gG protein, hepatitis B virus (HBV) core protein, Epstein-Barr virus (EBV) glycoprotein 125 (gp125), bacterial outer membrane protein assembly factor BamA, bacterial translocation assembly module protein TamA, bacterial polypeptide-transport associated protein domain protein, bacterial surface antigen D15, anthrax protective protein, anthrax lethal factor, anthrax edema factor, *Salmonella typhii* S1Da, *Salmonella typhii* S1Db, cholera toxin, cholera heat shock protein, *Clostridium botulinum* antigen S, *botulinum* toxin, *Yersinia pestis* F1, *Yersinia pestis* V antigen, *Yersinia pestis* YopH, *Yersinia pestis* YopM, *Yersinia pestis* YopD, *Yersinia pestis* plasminogen activation factor (Pla), *Plasmodium* circumsporozoite protein (CSP), *Plasmodium* sporozoite surface protein (SSP2/TRAP), *Plasmodium* liver stage antigen 1 (LSAT), *Plasmodium* exported protein 1 (EXP 1), *Plasmodium* erythrocyte binding antigen 175 (EBA-175), *Plasmodium* cysteine-rich protective antigen (cyRPA), *Plasmodium* heat shock protein 70 (hsp70), *Schistosoma* Sm29, and *Schistosoma* signal transduction protein 14-3-3.

Compositions for use in the invention may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, $19^{th}$ Edition, Mack Publishing Company, Eastern Pennsylvania, USA.

Compositions may be prepared together with a physiologically acceptable carrier or diluent. Typically, such compositions are prepared as liquid suspensions of cells. The cells may be mixed with an excipient which is pharmaceutically acceptable and compatible with the active ingredient. Suitable excipients are, for example, water, saline, dextrose, glycerol, of the like and combinations thereof In addition, if desired, the pharmaceutical compositions of the invention may contain minor amounts of auxiliary substances such as wetting or emulsifying agents, pH buffering agents, and/or adjuvants which enhance effectiveness. In one embodiment of the invention, the adjuvant comprises human serum albumin (HSA).

One suitable carrier or diluent is PlasmaLyte A™. This is a sterile, nonpyrogenic isotonic solution for intravenous administration. Each 100 mL contains 526 mg of Sodium Chloride, USP (NaCl); 502 mg of Sodium Gluconate ($C_6H_{11}NaO_7$); 368 mg of Sodium Acetate Trihydrate, USP ($C_2H_3NaO_2 3H_2O$); 37 mg of Potassium Chloride, USP (KCl); and 30 mg of Magnesium Chloride, USP ($MgCl_2 6H_2O$). It contains no antimicrobial agents. The pH is adjusted with sodium hydroxide. The pH is 7.4 (6.5 to 8.0).

As discussed above, the present invention also relates to a kit having at least two containers, comprising a vaccine in a first container and an adjuvant in a second container, wherein the adjuvant comprises a population of isolated allogeneic human mesenchymal stem cells. Any of the adjuvants or vaccines discussed herein may be formulated in a kit according to the present disclosure. In one embodiment of the invention the mesenchymal stem cells are not genetically manipulated. In another embodiment of the invention, the mesenchymal stem cells are cryopreserved in the second container. For example, the mesenchymal stem cells can be suspended in cryoprotectant consisting of Hespan® (6% hetastarch in 0.9% sodium chloride) supplemented with 2% HSA and 5% DMSO and then aliquoted into cryopreservation containers for placement in vapor phase nitrogen freezers. In another embodiment, the mesenchymal stem cells may be provided in the second container in PlasmaLyte A™ supplemented with 1% HSA. In another embodiment, the kit has at least three containers, wherein the third container comprises dilution buffer for mesenchymal stem cell suspension and dilution. In a further embodiment, the dilution buffer contains PlasmaLyte A™ supplemented with 1% HSA.

In one embodiment, the invention is a composition comprising an adjuvant and a vaccine in immunoprotective amounts. One of skill in the art may formulate suitable compositions from among the adjuvants and vaccines disclosed herein.

EXAMPLES

Example 1

Effects of Aging on E47 mRNA Expression in Human Peripheral Blood Derived B Cells As discussed above, both E47 and Pax-5 are important transcription factors in early development for the B-cell lineage and mature B cell function. It has been demonstrated that a putative regulatory region in the Aicda gene contains both E47 and Pax-5 binding sites, both indispensable for AID gene expression. The following experiment demonstrates that E47 expression decreases as a function of age and that E47 expression in B cells is positively correlated with AID expression. See FIGS. 1 and 2.

Figure 1A:
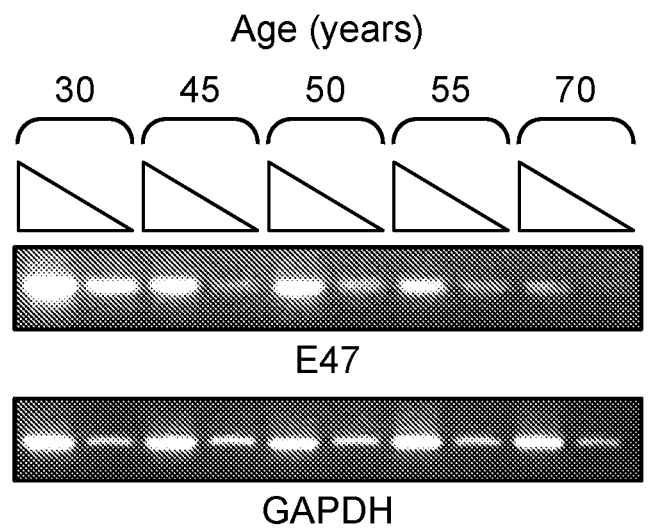
Figure 1B:
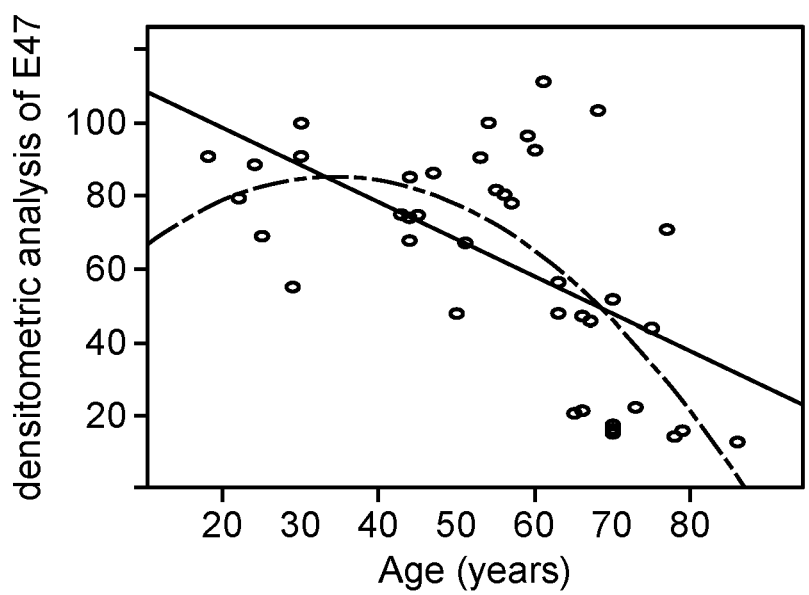

Forty-six subjects ranging in age from 20 to 85 years of age were recruited and peripheral blood was taken. $CD19^+$ B cells ($10^6$ cells/mL) were cultured with anti-CD40 (1 μg/mL) and IL-4 (10 ng/mL) for 24 hours. PCR was performed for E47 and GAPDH. E47 was normalized to GAPDH. FIG. 1 (A) shows undiluted and ¼ diluted RT-PCR from 5 representative subjects. In FIG. 1 (B), the graph shows densitometry analyses of CT's normalized to GAPDH. Numbers shown for each sample are percentages of the highest value taken as 100. Pearson's r value for the linear curve expressing correlation between age and E47 expression is r=−0.84, p=0.00001. Solid line refers to linear regression and dashed line refers to quadratic regression. Thus, the data shows that E47 expression decreases as a function of age.

Figure 2:
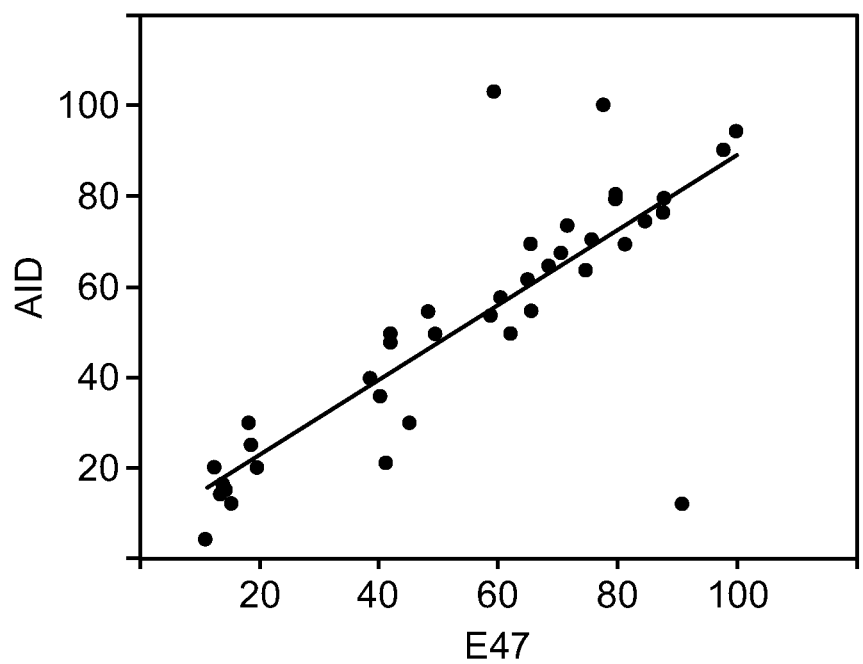

The blood from these subjects was also subjected to PCR for AID and GAPDH, and the results are shown in FIG. 2. E47 (from 24 hour stimulation) and AID (from 5 day stimulation) were individually normalized to their respective GAPDH value. Numbers shown for each sample are percentages of the highest value taken as 100. Data for E47 and AID PCR were positively correlated. Correlation is significant at the 0.01 level (2-tailed). Solid line refers to linear regression. E47 expression in B cells is positively correlated with AID expression as seen in FIG. 2. (r=0.80, p=0.01 level, 2-tailed).

Example 2

Switched Memory B Cells

Figure 3:
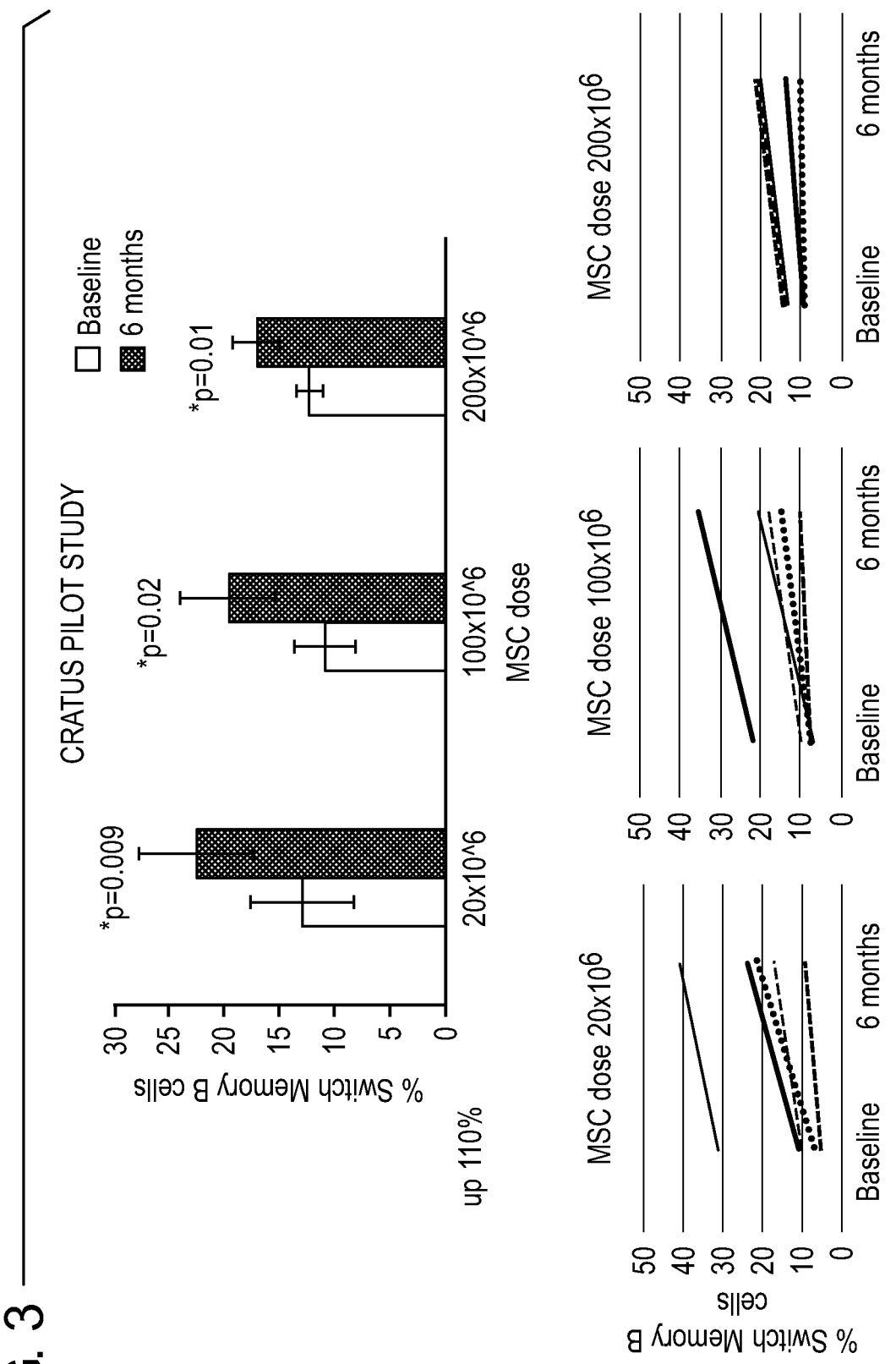
FIG. 3 shows the % of switched B cells as measured by flow cytometry. An increase in the % of switched memory B cells was observed in subjects who received 20×10$^6$, 100×10$^6$, or 200×10$^6$ mesenchymal stem cells at 6 months post-mesenchymal stem cell infusion as compared to the baseline measurement.

The following experiment shows that switched memory B cells increase in elderly subjects after treatment with allogeneic mesenchymal stem cells (MSC). Switched memory B cells have been measured at base line (prior to intravenous infusion of MSC) and 6 month post MSC infusion in human patients from the CRATUS test. The results show that MSC infusion upregulates the Switch memory B cell compartment which is a predictive biomarker for improved antibody response. See FIG. 3. This was true for the 3 doses of MSCs tested ($20\times10^6$, $100\times10^6$, or $200\times10^6$ mesenchymal stem cells). The data shows that intravenous administration of allogeneic mesenchymal stem cells augment by two-fold the Switch memory of B cells in some patients.

Figure 4:
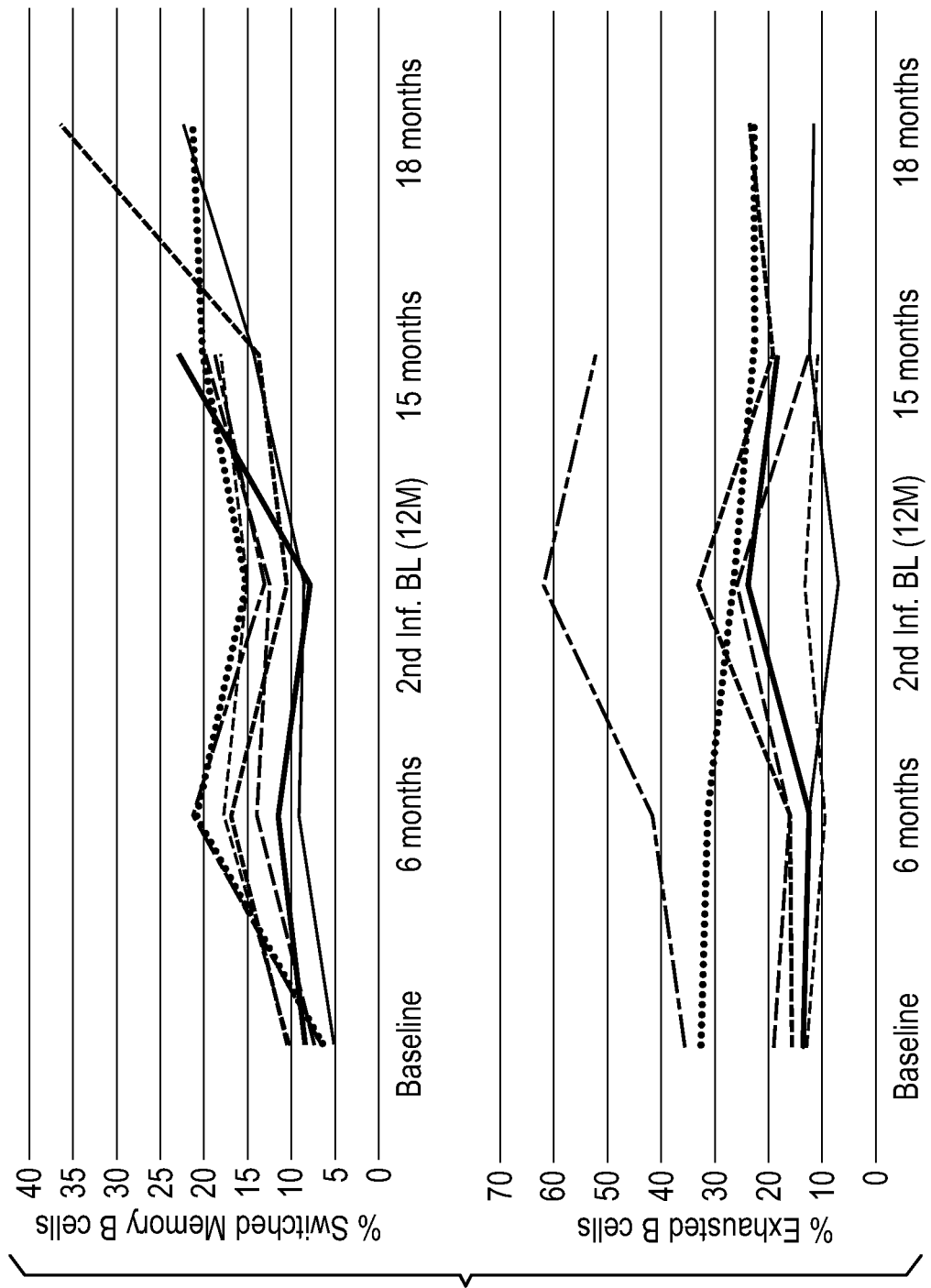
FIG. 4 shows the % of switched memory B cells and exhausted B cells as measured by flow cytometry. The % of switched memory B cells and exhausted B cells was measured in subjects who received a second mesenchymal stem cell infusion one year after their first mesenchymal stem cell infusion.

FIG. 4 shows the % of switched memory B cells and exhausted B cells in subjects who received a second mesenchymal stem cell infusion one year after their first mesenchymal stem cell infusion. The graphs suggest that a second injection at 12 months may be necessary to maintain the improvements on the immune cells derived from the initial mesenchymal stem cell treatment.

Example 3

T Cell Activation

Figure 5A:
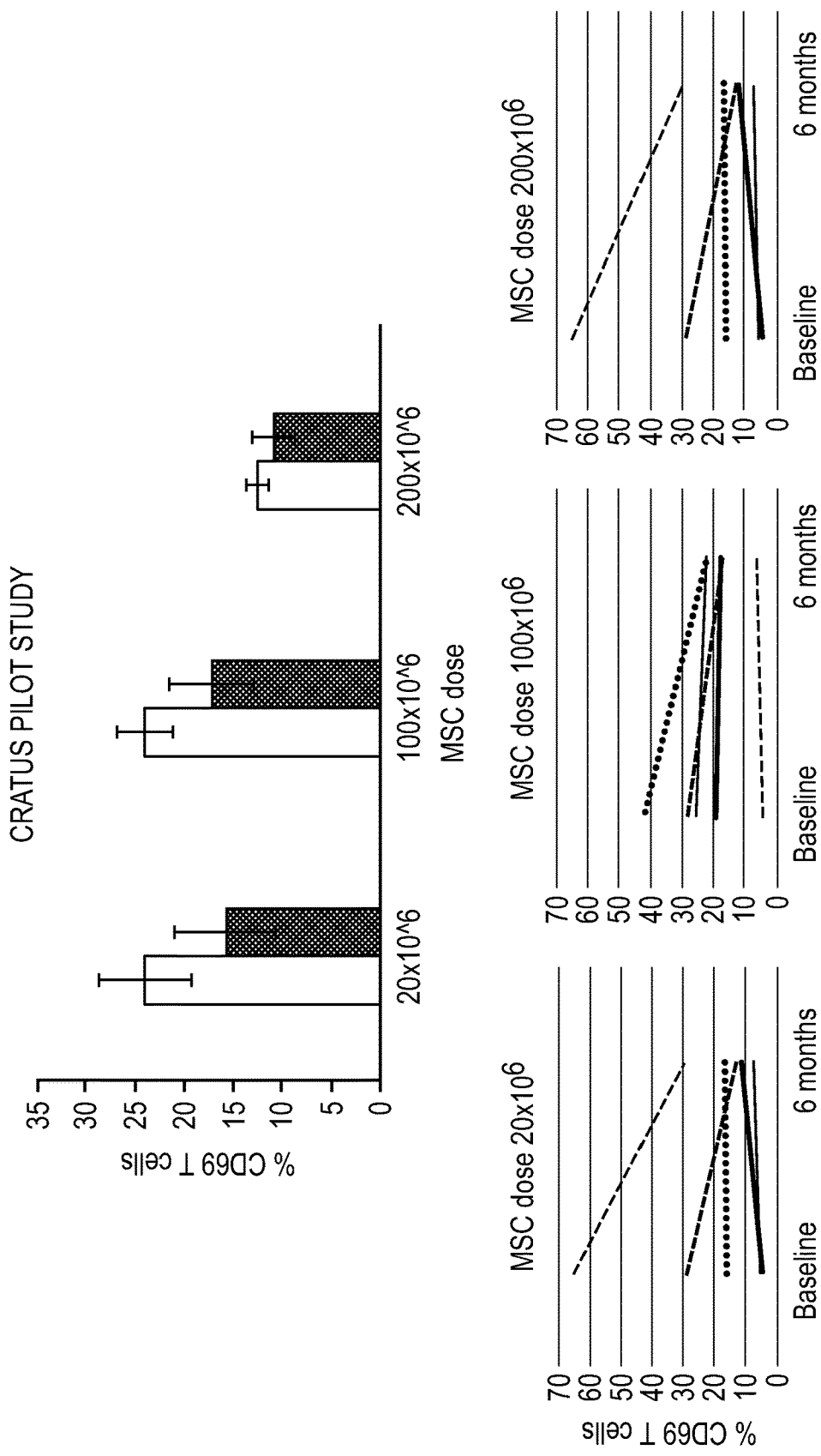
Figure 5B:
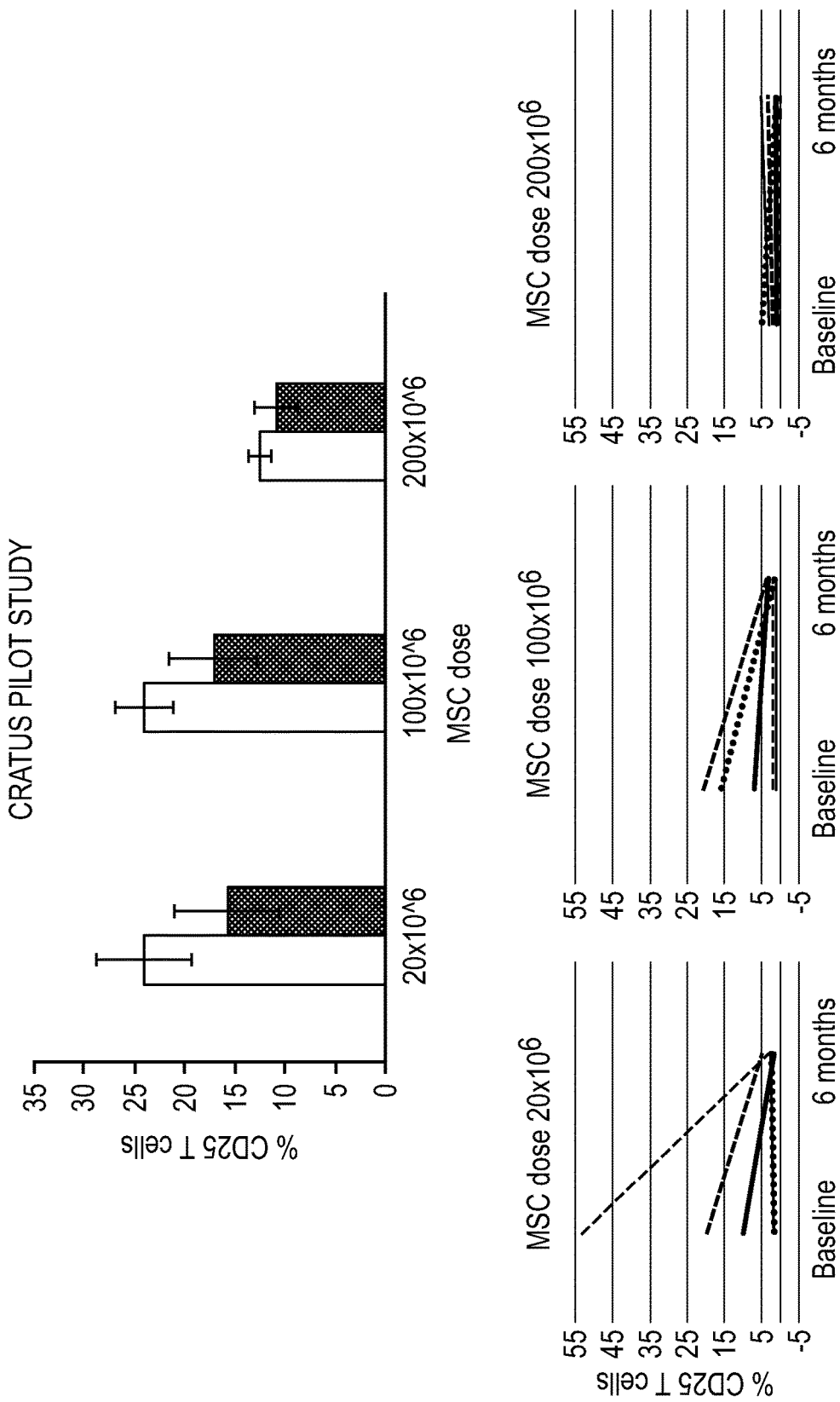
Figure 5C:
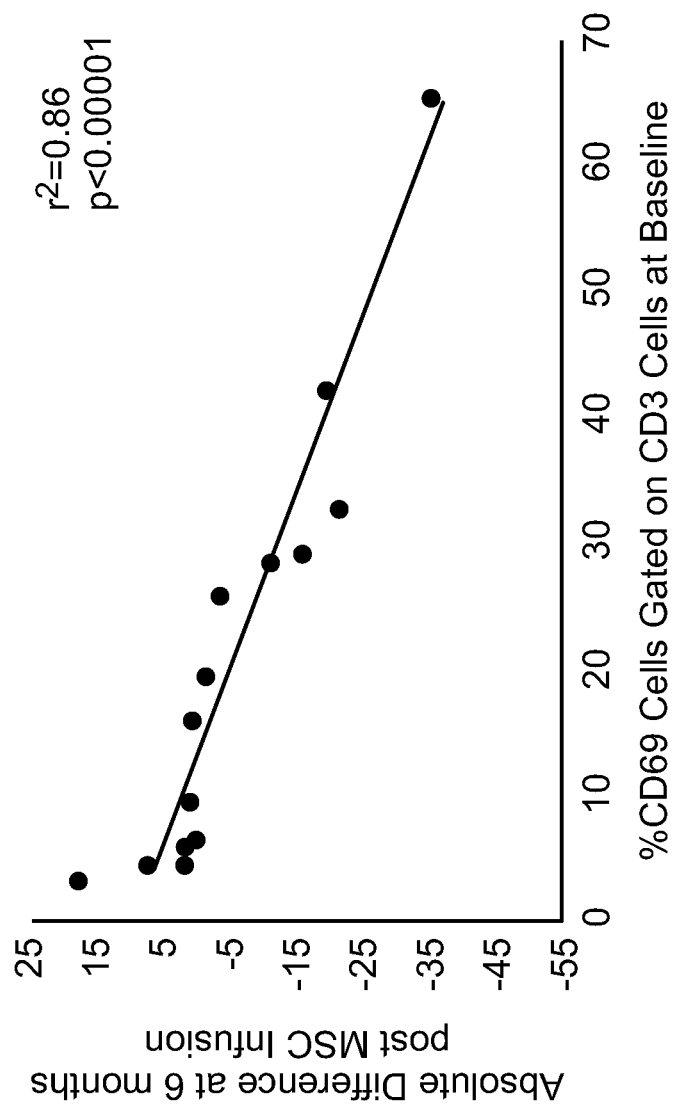
Figure 5D:
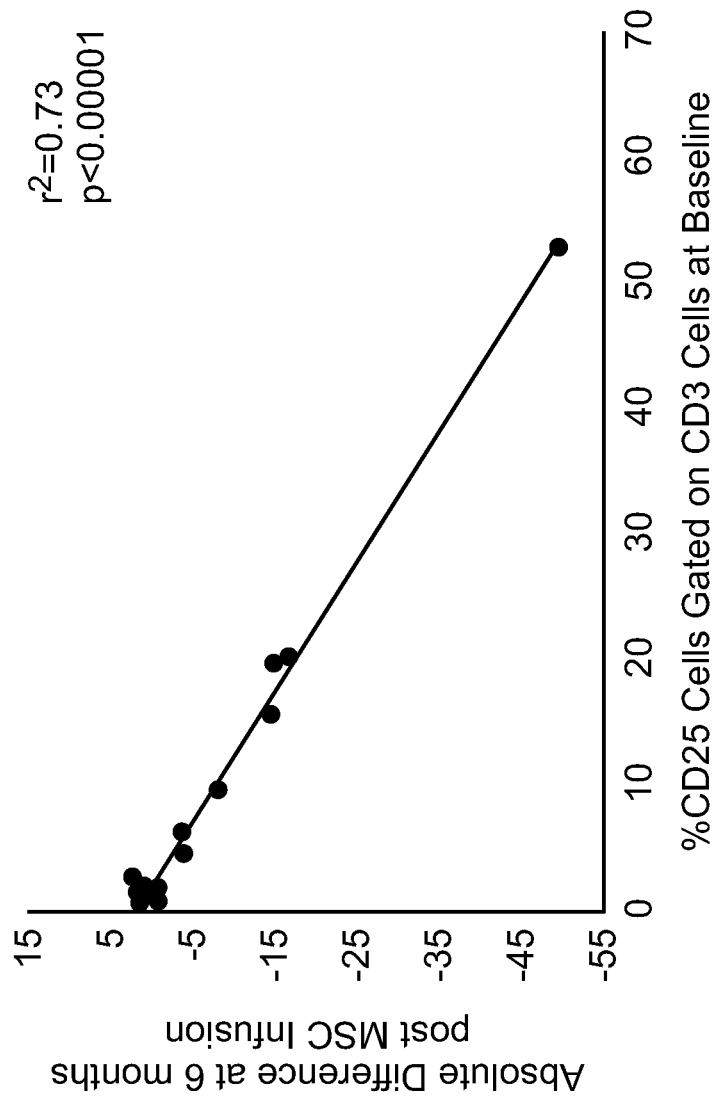

The following experiment shows that both early and late/chronic T cell activation decrease after allogeneic MSC treatment. The early marker of T cell activation (CD69) and the late/chronic marker of T cell activation (CD25) have been measured in human patients from the CRATUS test sample. As shown in FIGS. 5A and 5B, there is no T cell activation (rejection) induced by the allogeneic mesenchymal stem cells at any dose ($20\times10^6$, $100\times10^6$, or $200\times10^6$ mesenchymal stem cells). See also FIGS. 5C and 5D, which show the absolute difference at six months post MSC infusion against the % CD69 or % CD25 cells.

Example 4

Immune Risk Phenotype

The Immune Risk Phenotype was measured on the same CRATUS subjects undergoing a second MSC infusion one year post the first MSC infusion. See FIG. 6. The results show MSC infusion improves the $CD4^+$:$CD8^+$ T cell ratio. Furthermore, by 12 months post the first infusion the effects begin to regress. At that time, a second MSC infusion yields additional improvement. A second injection at 12 months may be necessary to maintain the improvements on the immune cells derived from the initial mesenchymal stem cell treatment.

Example 5

TNF-Alpha

TNF-α reduces AID. TNF-α was measured in samples from two CRATUS subjects by intracellular staining of B cells by flow cytometry and confirmed by qPCR. Results are shown at baseline (12 months post-first infusion of MSCs) and three months (three months post $2^{nd}$ infusion) as shown in FIGS. 7A and 7B. The results show downregulation of intracellular TNF-α in B cells by flow cytometry after mesenchymal stem cell infusion. These results were confirmed by qPCR.

Example 6

Effects of Intravenous Delivery of Allogeneic Human Mesenchymal Stem Cells on VaccinE-Specific Antibody Responses in Patients with Aging Frailty—The HERA Trial (Phase I/II)

The HERA Trial is a phase I/II randomized, double-blinded, and placebo-controlled study. The primary objective of the study is to demonstrate that intravenous administration of mesenchymal stem cells can improve adaptive immunity and can improve primary B cell response to the influenza vaccine in subjects with aging frailty.

Forty-three (43) subjects with aging frailty are enrolled. The adjuvant (allogeneic mesenchymal stem cells) are administered by peripheral intravenous infusion. The total duration for each subject after infusion is 12 months, plus up to an additional 2 months for the Screening and Baseline Visits. A Safety Run-In is followed by a Double-Blinded Randomized Phase. All subjects must meet the inclusion/exclusion criteria, and are evaluated prior to the scheduled infusion to establish the baseline.

The Safety Run-In

The Safety Run-In includes 23 subjects in 3 cohorts and is performed to determine the optimal time point to administer the influenza vaccine after mesenchymal stem cell infusion.

Cohort A (3 subjects): A single peripheral intravenous infusion of $20 \times 10^6$ mesenchymal stem cells is administered to teach subject. At 1 week post-infusion, the subjects receive a single 0.5 mL dose intramuscular injection of the Fluzone High-Dose vaccine (Sanofi Pasteur), which is recommended for patients ≥65 years of age. These subjects are infused first (i.e., prior to any subjects of Cohorts B and C), and are infused no less than 5 days apart.

Cohort B (10 subjects): A single peripheral intravenous infusion of $100 \times 10^6$ mesenchymal stem cells is administered to each subject. At 1 week post-infusion, the subjects receive a single 0.5 mL dose intramuscular injection of the Fluzone High-Dose vaccine.

Cohort C (10 subjects): A single peripheral intravenous infusion of $100 \times 10^6$ mesenchymal stem cells is administered to each subject. At 4 weeks post-infusion, the subjects receive a single 0.5 mL dose intramuscular injection of the Fluzone High-Dose vaccine.

The subjects of Cohorts B and C are randomized, and the first 3 subjects are infused no less than 5 days apart. Follow-up visits occur at 1 and 4 weeks post-vaccination, to determine safety and efficacy of the vaccination after mesenchymal stem cell infusion. After all 23 subjects are infused and vaccinated, a 30-day review is conducted to assess all safety data. The Double-Blinded Randomized Phase is conducted after the successful completion of the Safety Run-In has been reviewed and approved. After the Safety Run-In data has been analyzed, both at 1 week and 4 weeks post-vaccination, a standard vaccination time point is utilized for the Double-Blinded Randomized portion of the trial.

The Double-Blinded Randomized Trial

The Double-Blinded Randomized Trial includes 20 subjects in 2 cohorts. All subjects must meet the inclusion/exclusion criteria, and are evaluated prior to the scheduled infusion to establish baseline. The subjects are randomized at a ratio of 1:1 into 2 cohorts as follows:

Cohort 1 (10 subjects): A single peripheral intravenous infusion of $100 \times 10^6$ mesenchymal stem cells are administered to each subject. At the optimal time-point post-infusion (1 or 4 weeks, as determined in the Safety Run-In), the subjects receive a single 0.5 mL dose intramuscular injection of the Fluzone High-Dose vaccine.

Cohort 2 (10 subjects): A single peripheral intravenous infusion of placebo (PlasmaLyte A™ with 1% HSA) is administered to each subject. At the optimal time-point post-infusion (1 or 4 weeks, as determined in the Safety Run-In), the subjects will receive a single 0.5 mL dose intramuscular injection of the Fluzone High-Dose vaccine.

A phone-call follow-up is done at 1 day post-infusion and post-vaccination. In-office follow-up visits are conducted at Week 1 and Week 4 post-vaccination, and Month 6 and Month 12 post-infusion, to complete all safety and efficacy assessments. Any subjects that develop influenza-type symptoms during the first 7 months after the vaccination must immediately schedule an office visit, so that evaluation of the potential influenza strain can be assessed.

Primary Endpoint

The primary efficacy endpoint is B cell function as measured by (1) the ability of B cells to upregulate activation-induced cytidine deaminase (AID) in response to CpG or Influenza Vaccine through qPCR and (2) Influenza specific antibody production through HAI and ELISA. The data for the primary efficacy endpoint is obtained from the Baseline Visit, Vaccination Visit (performed at 1 or 4 weeks post-mesenchymal stem cell infusion), the Week 1 and Week 4 post-vaccination Follow-Up Visits, and the Month 6 and Month 12 post-infusion Follow-Up Visits.

Inclusion Criteria

All subjects enrolled in this trial must: provide written informed consent; be 65-95 years of age at the time of signing the Informed Consent Form; have a diagnosis of frailty, with a score of 4 to 7 using the Canadian Frailty Scale; show immunosenescence as measured by whole blood flow cytometry staining resulting in ≤5% switched memory B cells, late/exhausted memory at ≥10%, $CD8^+$ naïve cells ≤20%, and $CD8^+$ TEMRA cells ≥40%; and have total bilirubin between 0.3-1.9 mg/dL.

Adjuvant and Placebo

The final mesenchymal stem cell formulation is $2.5 \times 10^6$ mesenchymal stem cells/mL suspended in 80 mL of PlasmaLyte A™ containing 1.0% HSA for subjects to receive $100 \times 10^6$ mesenchymal stem cells. For subjects in the Run-In Phase who receive $20 \times 10^6$ mesenchymal stem cells, the final formulation is $0.5 \times 10^6$ mesenchymal stem cells/mL suspended in 80 mL PlasmaLyte A™ containing 1.0% HSA. The adjuvant is manufactured by Cell Processing Facility of Longeveron LLC (Life Sciences and Technology Park, 1951 NW 7$^{th}$ Ave., Miami, FL 33136).

Dilution buffer is used for placebo. The final formulation of placebo is PlasmaLyte A™ containing 1.0% HSA (total 80 mL).

Adjuvant Administration Dosage and Rate

Subjects in this trial receive a single infusion of $20 \times 10^6$ mesenchymal stem cells, $100 \times 10^6$ mesenchymal stem cells, or placebo. The maximum infusion rate is $2.5 \times 10^6$ mesenchymal stem cells/min, which is far below the maximum reported dosing rate. Table 3 provides a breakdown of the infusion parameters for the mesenchymal stem cell and placebo infusions. A total of 80 mL is delivered intravenously to each subject.

TABLE 3

Mesenchymal Stem Cell Dosing for the Randomized Study

| Total Mesenchymal Stem Cells Delivered | Total Volume (cells + PlasmaLyte A™ with 1% HSA) | Delivery Concentration (Mesenchymal Stem Cells/mL) | Delivery Rate (Mesenchymal Stem Cells/min) | Delivery Rate (mL/min) | Total Delivery Time (min) |
|---|---|---|---|---|---|
| 0 (placebo) | 80 mL | N/A | N/A | 2 | 40 |
| $20 \times 10^6$ cells | 80 mL | $0.25 \times 10^6$ | $0.5 \times 10^6$ | 2 | 40 |
| $100 \times 10^6$ cells | 80 mL | $1.25 \times 10^6$ | $2.5 \times 10^6$ | 2 | 40 |

What is claimed is:

1. A method of enhancing a subject's immune response to a vaccine or inducing an immune response in a subject whose immune system did not previously react to the vaccine administered, comprising:
   identifying a human subject exhibiting inflammaging and the syndrome of aging frailty and in need of treatment with a vaccine in combination with an adjuvant comprising allogeneic human mesenchymal stem cells,
   administering to the subject concurrently or sequentially the vaccine and the adjuvant,
   wherein the adjuvant is a population of isolated allogeneic human mesenchymal stem cells that have not been genetically manipulated;
   and wherein the allogeneic human mesenchymal cells are administered in an amount effective at reducing inflammaging.

2. The method of claim 1 wherein the intracellular TNF-α expression in B cells of the subject decreases by at least two-fold as compared to the TNF-α expression levels in B cells of the subject prior to administration of the adjuvant.

3. The method of claim 1 wherein the $CD4^+:CD8^+$ T cell ratio in the subject increases by at least two-fold as compared to the $CD4^+:CD8^+$ T cell ratio in the subject prior to administration of the adjuvant.

4. The method of claim 1 wherein the number of switched memory B cells in the subject increases by at least two-fold as compared to the number of switched memory B cells in the subject prior to administration of the adjuvant.

5. The method of claim 1 wherein the number of exhausted B cells in the subject decreases by at least two-fold as compared to the number of exhausted B cells in the subject prior to administration of the adjuvant.

6. The method of claim 1, wherein the mesenchymal stem cells are bone marrow-derived mesenchymal stem cells.

7. The method of claim 1, wherein the mesenchymal stem cells do not express STRO-1.

8. The method of claim 1, wherein the mesenchymal stem cells do not express CD45.

9. The method of claim 1, wherein the mesenchymal stem cells do not express fibroblast surface markers or have a fibroblast morphology.

10. The method of claim 1, wherein the vaccine comprises one or more inactivated viruses.

11. The method of claim 10, wherein the one or more inactivated viruses are selected from the group consisting of adenoviruses, picornaviruses, papillomaviruses, polyomaviruses, hepadnaviruses, parvoviruses, pox viruses, Epstein-Barr virus, cytomegalovirus (CMV), herpes virus, roseolovirus, varicella zoster virus, filoviruses, paramyxoviruses, orthomyxoviruses, rhabdoviruses, arenaviruses, coronaviruses, human enteroviruses, hepatitis A virus, human rhinovirus, polio virus, retroviruses, rotaviruses, flaviviruses, hepaciviruses, togaviruses, and rubella virus.

12. The method of claim 1, wherein the vaccine comprises an inactivated influenza virus.

13. The method of claim 1, wherein the adjuvant is administered at least yearly.

14. The method of claim 1, wherein the adjuvant is administered by infusion or direct injection.

15. The method of claim 1, wherein the adjuvant is administered intramuscularly, intravenously, intraarterially, intraperitoneally, subcutaneously, intradermally, orally, or intranasally.

16. The method of claim 1, wherein the adjuvant is administered at a dose of about $100 \times 10^6$ mesenchymal stem cells.

17. The method of claim 1, wherein the adjuvant is administered at a dose of about $200 \times 10^6$ mesenchymal stem cells.

18. The method of claim 1, further comprising administering a second injection of adjuvant at 12 months after the first injection of adjuvant.

19. The method of claim 1, wherein the adjuvant is administered sequentially with the vaccine.

20. The method of claim 19, wherein the adjuvant is administered at least 1 week before the vaccine.

21. The method of claim 1, wherein the adjuvant and vaccine are administered concurrently.

22. The method of claim 1, wherein the human mesenchymal stem cells are obtained from a human donor and a step of wherein major histocompatibility complex (MHC) matching of the human donor to the subject is not employed prior to administration of the vaccine and adjuvant to the subject.

* * * * *